United States Patent [19]

Walker et al.

[11] Patent Number: 5,773,464
[45] Date of Patent: Jun. 30, 1998

[54] C-10 EPOXY TAXANES

[75] Inventors: Michael A. Walker, Durham; John F. Kadow, Wallingford, both of Conn.

[73] Assignee: Bristol-Myers Squibb Company, Princeton, N.J.

[21] Appl. No.: 920,451

[22] Filed: Aug. 29, 1997

Related U.S. Application Data

[60] Provisional application No. 60/037,441, Feb. 7, 1997 and provisional application No. 60/027,398, Sep. 30, 1996.

[51] Int. Cl.[6] .................. A61K 31/335; C07D 315/00
[52] U.S. Cl. ..................... 514/475; 549/510; 549/511
[58] Field of Search ................................ 549/510, 511; 514/475

[56] References Cited

U.S. PATENT DOCUMENTS

| | | | |
|---|---|---|---|
| 4,814,470 | 3/1989 | Colin et al. | 514/449 |
| 4,960,790 | 10/1990 | Stella et al. | 514/449 |
| 5,248,796 | 9/1993 | Chen et al. | 549/510 |
| 5,254,580 | 10/1993 | Chen et al. | 514/449 |
| 5,272,171 | 12/1993 | Ueda et al. | 514/449 |
| 5,352,806 | 10/1994 | Gunawardana et al. | 549/510 |
| 5,395,850 | 3/1995 | Roth | 549/510 |

FOREIGN PATENT DOCUMENTS

| | | |
|---|---|---|
| 590267A2 | 4/1994 | European Pat. Off. . |
| 600517A1 | 6/1994 | European Pat. Off. . |
| 617034A1 | 9/1994 | European Pat. Off. . |
| 764643A1 | 3/1997 | European Pat. Off. . |
| 92/14813 | 6/1994 | France . |
| 2296239 | 6/1996 | United Kingdom . |
| WO93/02067 | 2/1993 | WIPO . |
| WO93/06093 | 4/1993 | WIPO . |
| WO94/08984 | 4/1994 | WIPO . |
| WO94/13655 | 6/1994 | WIPO . |
| WO94/14787 | 7/1994 | WIPO . |
| WO94/15599 | 7/1994 | WIPO . |
| WO94/15929 | 7/1994 | WIPO . |
| WO94/20485 | 9/1994 | WIPO . |
| WO95/33736 | 12/1995 | WIPO . |
| WO96/03394 | 2/1996 | WIPO . |

OTHER PUBLICATIONS

E.K. Rowinsky and R.C. Donehower, "The Clinical Pharmacology and Use of Antimicrotubule Agents in Cancer Chemotherapeutics," Pharmac. Ther., 52: 35–84, 1991.
C.M. Spencer and D. Faulds, "Paclitaxel, A Review of its Pharmacodynamic and Pharmacokinetic Properties and Therapeutic Potential in the Treatment of Cancer," Drugs, 48(5), 794–847, 1994.
K.C. Nicolaou, et al, "Chemistry and Biology of Taxol," Angew. Chem., Int. Ed. Engl., 33:15–44, 1994.
Greene and Wuts, Protective Groups in Organic Synthesis, 2nd Ed., John Wiley & Sons, and McOmie, 1991.
Protective Groups in Organic Chemistry, Ed. J.F.W. McOmie, Plenum Press, 1973.

S.–H. Chen, et al, "First Syntheses of Novel Paclitaxel (Taxol) Analogs Modified at the C4–Position," J. Org. Chem., 59, pp. 6156–6158, 1994.
S.–H. Chen, et al, "Structure–Activity Relationships of Taxol: Synthesis and Biological Evaluation of C2 Taxol Analogs," Bioorganic and Medicinal Chemistry Letters, vol. 4, No. 3, pp. 479–482, 1994.
R.A. Johnson, "Taxol Chemistry. 7–O–Triflates as Precursors to Olefins and Cyclopropanes," Tetrahedron Letters, vol. 35, No. 43, pp. 7893–7896, 1994.
X. Liang and G.I. Kingston, "Synthesis and Biological Evaluation of Paclitaxel Analogs Modified in Ring C," Tetrahedron Letters, vol. 36, No. 17, pp. 2901–2904, 1995.
G. Roth, et al, "Reaction of Paclitaxel and 10–Desacetyl Baccatin III with Diethylamino Sulfurtrifluoride," Tetrahedron Letters, vol. 36, No. 10, pp. 1609–1612, 1995.
S.–H. Chen, et al, "The Chemistry of Taxanes: Reaction of Taxol and Baccatin Derivatives with Lewis Acids in Aprotic and Protic Media," Tetrahedron, vol. 49, No. 14, pp. 2805–2828, 1993.
L.L. Klein, "Synthesis of 9–Dihydrotaxol: A Novel Bioactive Taxane, " Tetrahedron Letters, vol. 34, No. 13, pp. 2047–2050, 1993.
Physician's Desk Reference, 49th Edition, Medical Economics, p. 682, 1995.
J. Kant, et al, "A Chemoselective Approach to Functionalize the C–10 Position of 10–Deacetylbaccatin III. Synthesis and Biological Properties of Novel C–10 Taxel Analogues," Tetrahedron Letters, 35, No. 31, pp. 5543–5546, 1994.
S.G. Arbuck, et al, Taxol® Science and Applications, edited by M. Suffness, 1995 (CRC Press Inc., Boca Raton, Florida), pp. 379–415.
K. C. Nicolaou, et al, "Chemical Synthesis and Biological Evaluation of C–2 Taxoids," J. Am. Chem. Soc., 117, pp. 2409–2420, 1995.
K. V. Rao, et al, "Synthesis and Evaluation of Some 10–Mono–and 2',10–Diesters of 10–Deacetylpaclitaxel," J. Med. Chem., 38, pp. 3411–3414, 1995.
G. I. Georg, et al, "Stereoselective Synthesis of 9β–Hydroxytaxanes Via Reduction With Samarium Diiodide," Tetrahedron Letters, 36(11), pp. 1783–1786, 1995.
F.A. Holmes, et al, Taxane Anticancer Agents Basic Science and Current Status, edited by G.I. Georg, et al, 1995, American Chemical Society, Washington, D.C. 31–57.
G.I. Georg, et al, J. Org. Chem., 59, pp. 4015–4018, 1994.
S.J. Danishefsky, et al, J. Amer. Chem. Soc., 118, pp. 2843–2859, 1996.
M. Menichincheri, et al, Med. Chem. Research, 5, pp. 534–555, 1995.
G.C.B. Harriman, et al, Tetrahedron Letters, 36(49), pp. 8909–8912, 1995.

(List continued on next page.)

*Primary Examiner*—Bernard Dentz
*Attorney, Agent, or Firm*—Samuel J. DuBoff

[57] ABSTRACT

The present invention concerns novel paclitaxel derivatives, their use as antitumor agents, and pharmaceutical formulations.

22 Claims, No Drawings

OTHER PUBLICATIONS

A. Datta, et al, Tetrahedron Letters, 36(12), pp. 1985–1988, 1995.

David G.I. Kingston, et al, J. of Natural Products, 53(1), pp. 1–12, 1990.

C.R. Johnson, Accounts of Chemical Res., 6, pp. 341–347, 1973.

C.R. Johnson and R.C. Elliott, J. Amer. Chem. Soc., 104, pp. 7041–7044, 1982.

H. Bouchard, et al, Tetrahedron Letters, 35(52), pp. 9713–9716, 1994.

T.L. Riss, et al, "Comparison of MTT, XTT, and a Novel Tetrazolium Compound MTS for In–Vitro Proliferation and Chemosensitivity Assays," Mol. Biol. Cell 3 (Suppl.), 184a, 1992.

C-10 EPOXY TAXANES

BACKGROUND OF THE INVENTION

This application claims priority under 35 U.S.C. 119(e) from Provisional Applications 60/037,441 filed Feb. 7, 1997 and 60/027,398 filed Sep. 30, 1996.

1. Field of the Invention

The present invention concerns antitumor compounds. More particularly, the invention provides novel paclitaxel derivatives, pharmaceutical formulations thereof, and their use as antitumor agents.

2. Background Art

Taxol® (paclitaxel) is a natural product extracted from the bark of Pacific yew trees, Taxus brevifolia. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutics," Pharmac. Ther., 52:35–84, 1991; by Spencer and Faulds in "Paclitaxel, A Review of its Pharmacodynamic and Pharmacokinetic Properties and Therapeutic Potential in the Treatment of Cancer," Drugs, 48 (5) 794–847, 1994; by K. C. Nicolaou et al. in "Chemistry and Biology of Taxol," Angew. Chem., Int. Ed. Engl. 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, D.C., 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named Taxotere® (docetaxel) has also been found to have good antitumor activity. The structures of paclitaxel and Taxotere® are shown below along with the conventional numbering system for molecules belonging to the class; such numbering system is also employed in this application.

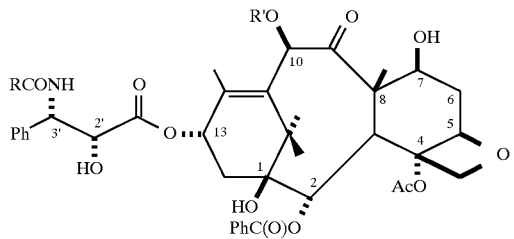

Taxol®: R=Ph; R'=acetyl
Taxotere®: R=t-butoxy; R'=hydrogen

SUMMARY OF THE INVENTION

This invention relates to novel antitumor compounds represented by formula I, or pharmaceutically acceptable salts thereof

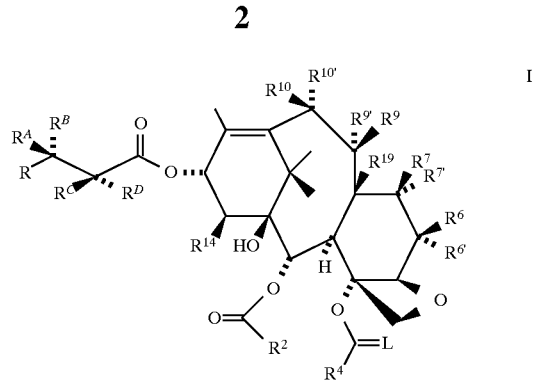

wherein:
R is phenyl, p-fluorophenyl, $C_{3-6}$ cycloalkyl, $C_{1-6}$ alkyl or $C_{1-6}$ alkenyl;
$R^A$ is hydrogen;
$R^B$ is independently —NHC(O)Ph or —NHC(O)O-($C_{1-6}$ alkyl);
$R^C$ is hydrogen;
$R^D$ is hydroxy;
$R^2$ is phenyl;
$R^4$ is methyl;
L is O;
$R^6$ and $R^{6'}$ are each hydrogen;
$R^{7'}$ is hydrogen; $R^7$ is hydrogen, hydroxy, —OCH$_2$OCH$_3$, —OCH$_2$SCH$_3$ or when taken together with $R^{19}$ forms a cyclopropane ring.
$R^9$ and $R^{9'}$ together form an oxo (keto) group;
$R^{10}$ and $R^{10'}$ together form an epoxide group which can be optionally substituted with $C_{1-6}$ alkyl;
$R^{14}$ is hydrogen; and
$R^{19}$ is methyl or when taken together with $R^7$ forms a cyclopropane ring.

Another aspect of the present invention provides a method for inhibiting tumor in a mammalian host which comprises administering to said mammalian host an antitumor effective amount of a compound of formula I.

Yet, another aspect of the present invention provides a pharmaceutical formulation which comprises an antitumor effective amount of a compound of formula I in combination with one or more pharmaceutically acceptable carriers, excipients, diluents or adjuvants.

DETAILED DESCRIPTION

In the application, unless otherwise specified explicitly or in context, the following definitions apply. The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, cyano, azido, $C_{1-6}$ alkylamino, di-$C_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis* 2d Ed., 1991, John Wiley & Sons, and McOmie; and *Protective Groups in Organic Chemistry* 1975, Plenum Press.

"Ph" means phenyl; "ipr" means isopropyl; "DAST" means diethylamino sulfur trifluoride.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

The term "taxane" or "taxane core" refers to moieties with a framework of the structure:

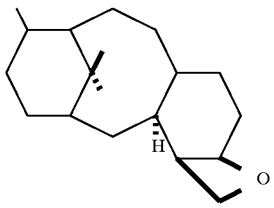

A number of reports of C-10 taxane analogs have appeared in the literature. Taxanes with alkyl substituents at C-10 have been reported in a published PCT patent application WO 9533740-A1. For making C-10 epi hydroxy or acyloxy compounds see PCT application WO 96/03394.

Other C-10 analogs have been reported in Tetrahedron Letters 1995, 36(12), 1985–1988; J. Org. Chem. 1994, 59, 4015–4018 and references therein; K. V. Rao et. al. Journal of Medicinal Chemistry 1995, 38 (17), 3411–3414; J. Kant et. al. Tetrahedron Lett. 1994, 35(31), 5543–5546; WO 9533736; WO 93/02067; U.S. Pat. No. 5,248,796; WO 9415929; and WO 94/15599.

To date, no taxane analogs possessing an exocyclic epoxide at the 10 position of the taxane core such as depicted in formula I have been reported in the literature nor has their use as anticancer agents been suggested.

Danishefsky et.al. (J. Am Chem. Soc. 1996, 118, 2843–2859) unsuccessfully utilized the epoxide intermediate depicted below as a synthetic intermediate in studies aimed at the total synthesis of baccatin and paclitaxel. In this same paper, Danishefsky et. al. also mention formation of another epoxide in a different intermediate as an unwanted side reaction.

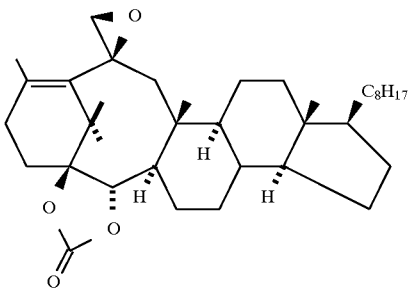

The cyclopropane group which can be constituted from $R^7$ and $R^{19}$ of formula I can alternatively be referred to as "7b,8b-methano" group as in Tetrahedron Letters, Vol 35, No 43, pp 7893–7896 (1994) or as "cyclopropa" group as in U.S. Pat. No. 5,254,580 issued Oct. 19, 1993.

Taxanes containing epoxides at the 6,7 position of the molecule have been described several times Tetrahedron Letters, 1995, 36(17), pp. 2901–2904; M. Meninchincheri et. al. Med. Chem. Research 1995, 5, pp. 534–555; U.S. Pat. No. 5,395,850-A; and British patent GB 2296239. These are of course totally different analogs.

Also taxanes which are deoxygenated at the 10 position and which contain an 11,12-epoxide have also been reported G. C. Harriman et. al. Tetrahedron Letters 1995, 36(49), pp. 8909–8912.

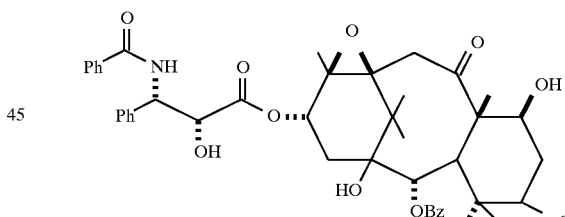

The new products that have the general formula I display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by techniques from the conventional organic chemistry repertoire. Schemes I–XII, which depict processes that compounds within the scope of formula I can be made, are only shown for the purpose of illustration and are not to be construed as limiting the processes to make the compounds by any other methods.

One method for preparing C-10 epoxy taxanes of formula I utilizes C-9,10 diketo taxanes as a key intermediate. The synthesis of a protected 9,10-diketo taxane (Scheme 1, compound V) has been reported by A. Datta et. al. in Tetrahedron Letters 1995, 36(12), 1985–1988. This preparation is essentially the same as that described in Scheme I with only very minor differences. A similar oxidation of the C-10 position has been reported by Bombardelli et. al. in PCT published patent application WO 96/03394 which was published on Feb. 8, 1996. A 9,10 diketo taxane was isolated by Kingston et. al. Journal of Natural Products, 1990, 53(1), pp. 1–12.

Intermediates V can be prepared using different protecting groups or via slightly different methods which are by now well known int the art. The hydrazinolysis of the C-10 acetate could be carried out prior to protection of paclitaxel. A taxane either unprotected or suitably protected at C7 and C-10 could undergo reductive removal of the sidechain to furnish a baccatin which could be reattached to alternate sidechains using standard methodology and protection schemes.

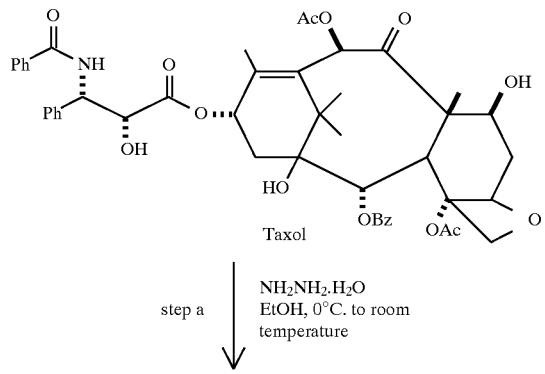

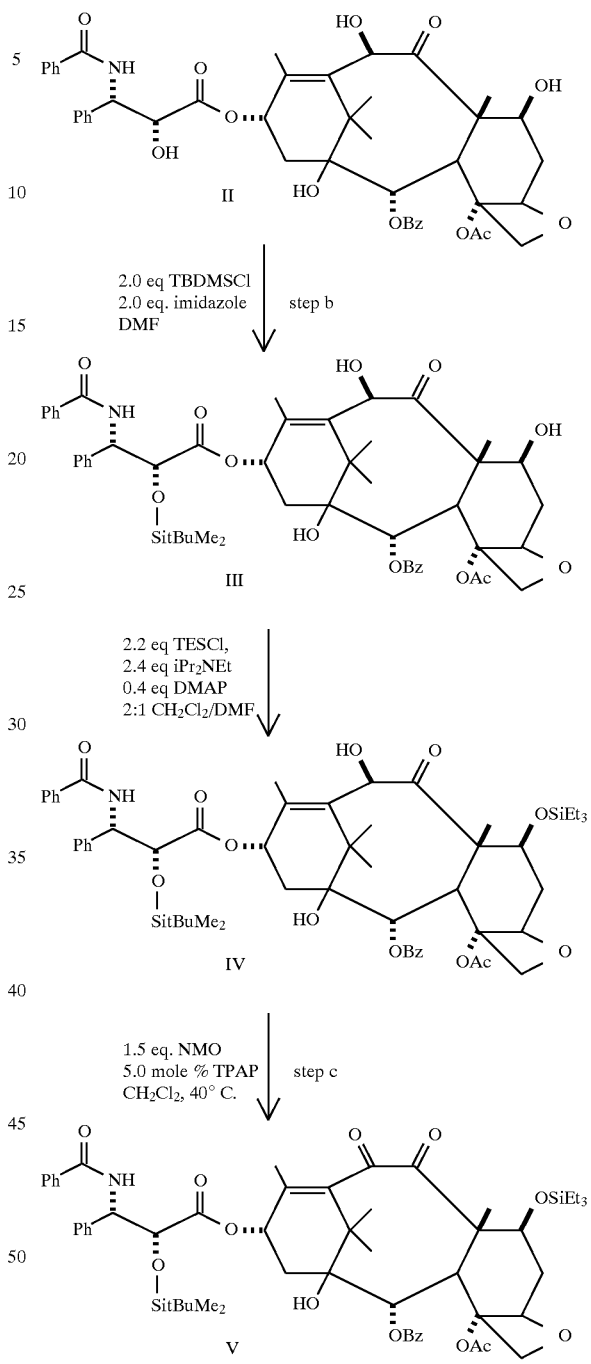

The following procedures describe methods which can be utilized to prepare taxane analogs of structure I.

One method for installation of the epoxide moiety is shown in Scheme 2, step d. Reaction of diketone V with from 1 to 5 equivalents of dimethylsulfonium methylide produces a single epoxide as a major product. Other ylides or temperatures may also be utilized and may produce epoxides of alternate stereochemistry and substitution, for example dimethyloxosuiphonium methylide, or substituted salts of N,N-dimethyl sulfoximines (C. R. Johnson Accounts of Chemical Research 1973, 6, 341). For a brief overview of all these and other ylides and primary references see "Some Modern Methods of Organic Synthesis, 2nd edition" by W. Carruthers Cambridge University Press, 1978, pp.106–127. Alternatively, the epoxides could be generated by a two step procedure: the first step being conversion of the C-10 ketone into an olefin using any number of reagents such as methylene triphenyl phosphine (for a brief overview and primary references see "Some Modern Methods of Organic Synthesis, 2nd edition" by W. Carruthers Cambridge University Press, 1978, pp.106–127.), the anion of phenylmethyl sulfoximine (C. R. Johnson Accounts of Chemical Research 1973, 6, 341), Peterson type olefinating reagents (for a brief overview and primary references see "Some Modern Methods of Organic Synthesis, 2nd edition" by W. Carruthers Cambridge University Press, 1978, pp. 318–329), or P-(alphalithioalkyl)phosphinothioic amides (C. R. Johnson and R. C. Elliot J.Am. Chem. Soc. 1982, 104(25), 7041). The second step of the sequence is oxidation of the olefin to the epoxide using a peracid such as m-chloroperbenzoic acid, m-nitroperbenzoic acid, peracetic acid, or trrfluoromethyl peracetic acid.

The silyl protecting groups may be removed (step e) using standard methodologies such as using pyridine hydrogen fluoride. Alternative methods are those such as using aqueous hydrochloric acid or tetrabutylammonium fluoride at below ambient temperature preferably −10° C. to 0° C. could be used for deprotection. Other protecting groups which could easily have been utilized in place of the silyl groups such as a benzyl chloroformate or a 2,2,2-trichloroethyl chloroformate could be removed by Hydrogenation or Zinc/acetic acid respectively.

Scheme 3 describes the synthesis of a Compound Ie which contains a C-7 methoxymethyl ether moiety. In Scheme 3, the C-7 alcohol is converted to a methylthio methyl ether moiety using dimethyl sulfide (DMS) and benzoyl peroxide to give intermediate VIII. Alternatively the reagent chloromethyl methyl sulfide and a tertiary amine base such as diisopropyl ethyl amine in an inert solvent such as dichloromethane could have been utilized to carry out the formation of the methylthio methyl ether VIII. Methylthio methyl (MTM) ether VIII can be desilylated using standard methodology to provide the 10-epoxy-7-MTM analogs I for use as antitumor agents. In Scheme 3, the methylthio methyl ether is converted to a methoxy methyl (MOM) ether using methanol and iodine. Alternatively, N-iodosuccinimide and stoichiometric methanol in an inert solvent such as dichloromethane could be utilized. Sometimes silver trifluoromethanesulfonate is also added to the later conditions to help insure smooth reaction. Finally, the methoxy methyl ether IX could be directly obtained by reacting alcohol VII in an inert solvent such as dichloromethane with excess chloromethyl methyl ether in the presence of an even greater excess of a tertiary amine base such as diisopropyl ethyl amine. This reaction could be carried out at room temperature or at higher temperatures. The deprotection of the 2' silyl group of intermediate IX to obtain compound Ie can be effected using tetrabutylammonium fluoride (TBAF), any of the conditions described above for Scheme 2 or any of the other deprotections used in the taxane art. Alternatively, other protecting groups, rather than silicon based moieties can be utilized.

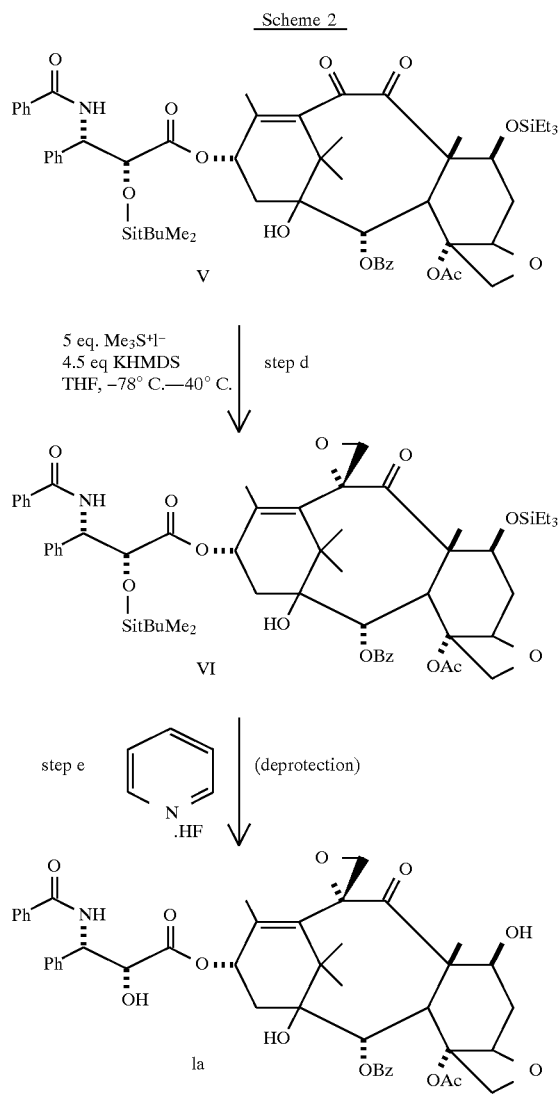

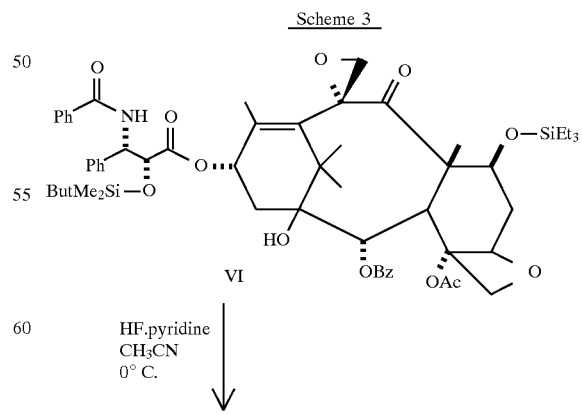

-continued
Scheme 3

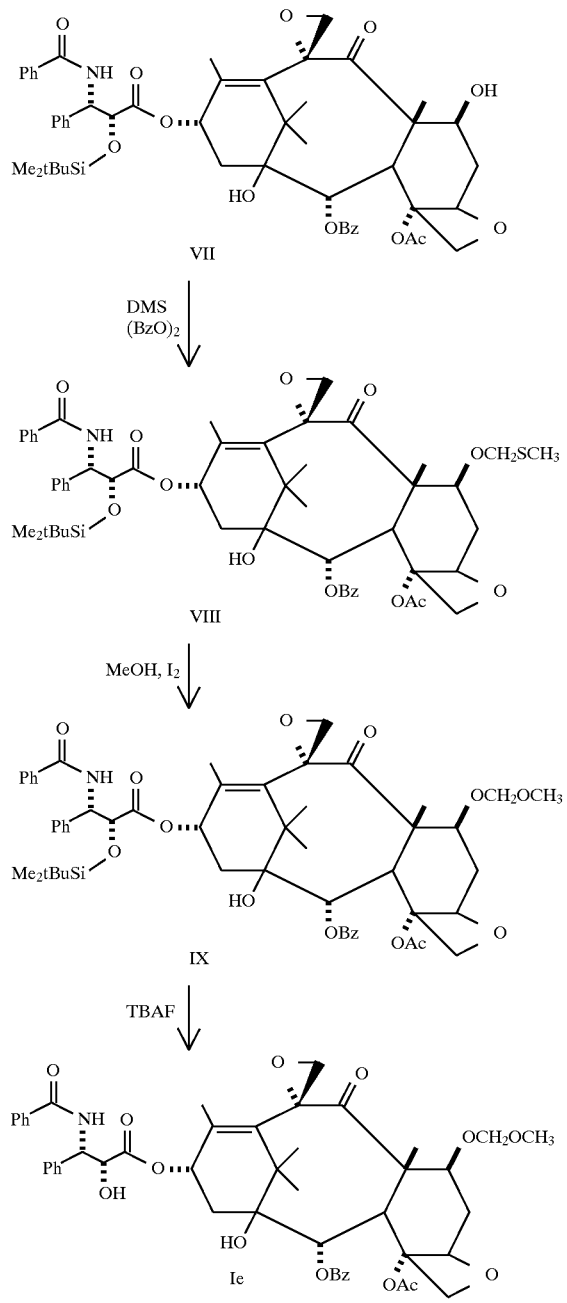

The synthesis of 7,19 cyclopropane containing taxane analogs with a free C-10 hydroxy group is described in H. Bouchard et. al. Tetrahedron Letters, 1994, 52, pp9713; and J. B. Hester et.al. PCT application WO 94/13655; and French patent Application 92/14813; and by Chen et. al. in U.S. Pat. No. 5,254,580.

A taxane of structure X (Scheme 4) prepared using the methodology in the above mentioned references is the starting material for the synthesis of C-10 epoxy-7,19- cyclopropane containing analogs I. The 2' hydroxy group of the sidechain can be protected as shown in Scheme 4 to produce intermediate XI. The preferred protecting group is is the t-butyl-dimethylsilyl ether but others may be utilized effectively.

Oxidation of the C-10 hydroxy group proceeds as described in earlier examples. Oxidation may be carried out using a number of methods but the preferred method is the TPAP oxidation which is shown in Scheme 4 to produce diketone XII. The diketone XII is then reacted with the epoxidizing reagents described above. Dimethylsulfonium methylide is a particularly effective one but others may be utilized. As shown in Scheme 4, epoxidation produces the C-10 epoxide XIII. Standard deprotection conditions as described above are then utilized to remove the 2' protecting group and produces compounds I containing a 7,19 cyclopropane moiety. The synthesis of compound Ij is shown in the example but other compounds with alternate sidechains or funtionality which are known in the art can be prepared in a similar manner.

C-7 deoxy-C-7,19-cyclopropane taxane analogs can be made using a similar sequence but the starting material would be a C-10 hydroxy-C-7 deoxy taxane rather than a C-10-hydroxy-C7,19 cyclopropane containing taxane. The preparation of 7-deoxy taxanes is well precedented in the taxane art and the references are described in the following section.

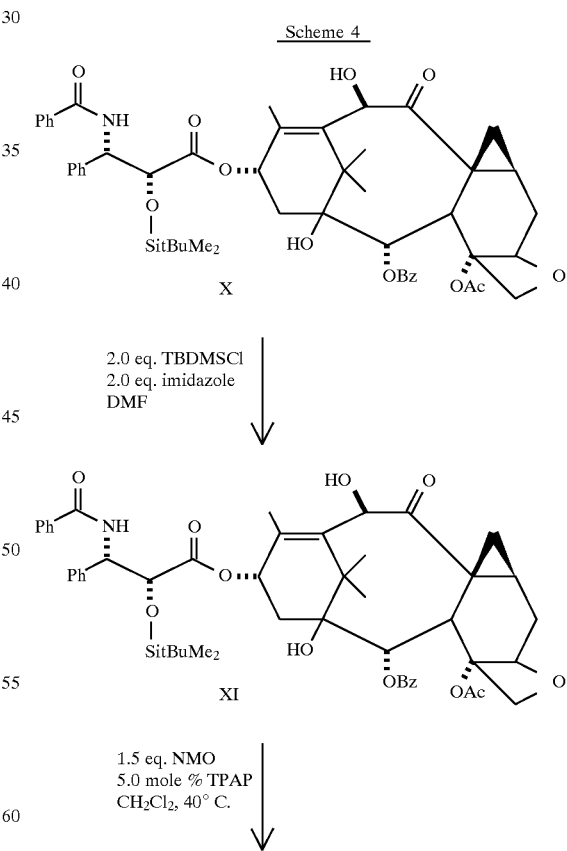

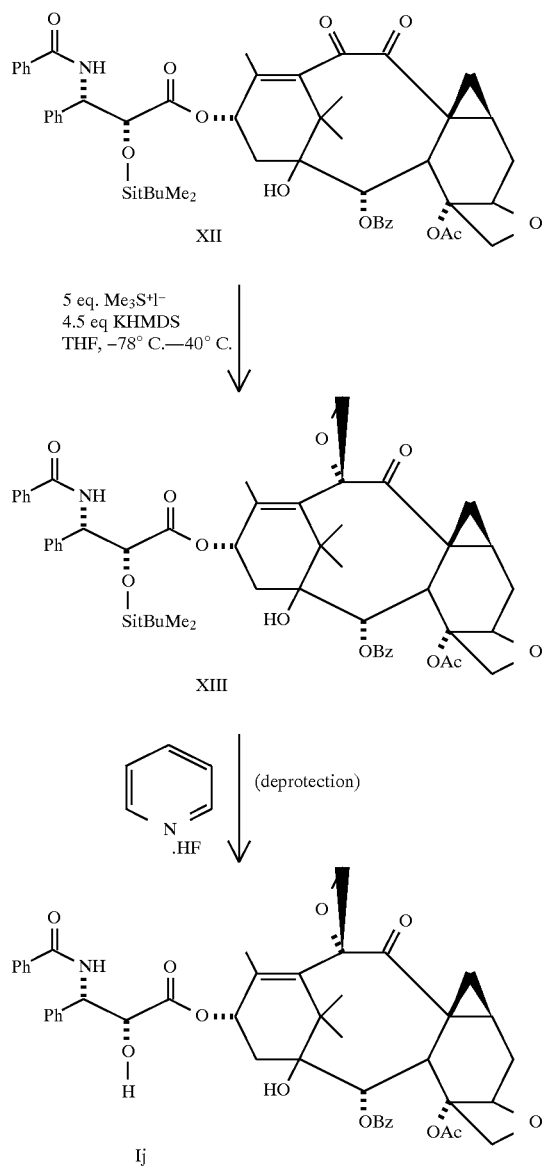

Some of the schemes refer to a hydroxy protecting group, preferably trialkylsilyl group. It is to be understood that hydroxy protecting group may be a carbonate or ester group. Thus when such a group is employed as a hydroxy protecting group, it may either be removed to generate the free hydroxy protecting group or it may remain as a part of the final product.

By now there are many publications teaching the introduction of a wide variety of groups onto a taxane core. By using these well established methods or obvious variants thereof, the starting taxanes of formula I, or hydroxy protected analogues thereof, can be readily made. For example, for transforming C4-acetoxy into other functional groups see, S. H. Chen et al., *J. Organic Chemistry*, 59, pp 6156–6158 (1994) and PCT application WO 94/14787 published Jul. 7, 1994; for converting C2-benzoyloxy to other groups see, S. H. Chen et al, *Bioorganic and Medicinal Chemistry Letters*, Vol. 4, No. 3, pp 479–482 (1994); K. C. Nicolaou et al., *J. Am. Chem. Soc.*, 1995, 117, 2409 and European Patent Application 617,034A1 published Sep. 28, 1994; for making C10 and/or C7 unsubstituted (deoxy) derivatives see, European Patent Application 590,267A2 published Apr. 6, 1994 and PCT application WO 93/06093 published Apr. 1, 1993; for making 7β,8β-methano, 6α,7α-dihydroxy and 6,7-olefinic groups see, R. A. Johnson, *Tetrahedron Letters*, Vol. 35, No 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and G. I. Kingston, *Tetrahedron Letters*, Vol. 36, No. 17, pp 2901–2904 (1995); for making C7-epi-fluoro see, G. Roth et al, *Tetrahedron Letters*, Vol 36, pp 1609–1612 (1995); for forming C7 esters and carbonates see, U.S. Pat. No. 5,272,171 issued Dec. 21, 1993 and S. H. Chen et al., *Tetrahedron*, 49, No. 14, pp 2805–2828 (1993); for 9a- and 9b-hydroxy taxanes see, L. L. Klein, *Tetrahedron Letters*, Vol 34, No 13, pp 2047–2050 (1993), PCT application WO 94/08984 published Apr. 28, 1994, U.S. Pat. No. 5,352,806 issued Oct. 4, 1994, PCT application WO 94/20485 published Sep. 15, 1994, and G. I. Georg et. al.. *Tetrahedron Letters*, Vol 36, No 11, pp 1783–1786 (1995).

DESCRIPTION OF SPECIFIC EMBODIMENTS

The specific examples that follow illustrate the syntheses of the compounds of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (d) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); (DHQ)$_2$PHAL (hydroquinine 1,4-phthalazinediyl diether). Tf is triflate or trifluoromethanesulfonate; LRMS (low resolution mass spectrometry); ESI (electrospray ionization); TBDMSCl is t-butyldimethylsilylchloride; DMF is dimethylforamide; TESCl is triethylsilylchloride; TPAP is tetrapropylammonium perruthenate; KHMDS is potassium hexamethyldisilazane.

Preparation of Starting Materials (Scheme 1)

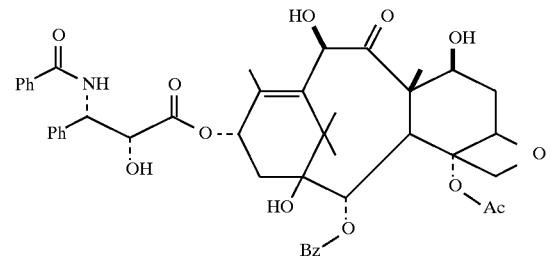

Compound II Taxol was suspended in 140 mL of EtOH and cooled to 0° C. To this was added 3.3 mL of hydrazine hydrate and the resulting solution stirred for 15 min. before removing the ice-bath. After stirring for 2 hours an additional 3.3 mL of hydrazine hydrate was added. The reaction was allowed to proceed until all starting material had been consumed. The mixture was transferred to a separatory funnel, diluted with Et$_2$O, and washed with H$_2$O (2×'s). The organic layer was dried over Na$_2$SO$_4$, filtered and solvent removed under vacuum to give the crude product which was purified by column chromatography (4.5×10 cm SiO$_2$, 60:40–75:25 EtOAc/Hexanes) to yield compound II as a solid. ESI-MS, Calcd for C$_{45}$H$_{49}$NO$_{13}$: 811.32. Found: 812.4 (M+H)$^+$. $^1$H NMR (300 MHz) d: 1.04 (s, 3), 1.14 (s, 3), 1.68 (s, 3), 1.70 (s, 3), 1.80–2.60 (overlapping m, 4), 2.32 (s, 3), 2.81 (d, 1, J=7.5), 3.82 (d, 1, J=6.9), 4.12–4.25 (overlapping m, 3), 4.38 (s, 1), 4.75 (m, 1), 4.87 (d, 1, J=9.3), 5.18 (s, 1), 5.6 (d, 1, J=6.8), 5.71 (m, 1), 6.13 (t, 1, J=8.3), 7.28–7.61 (overlapping m, 11), 7.71 (d, 2, J=7.3), 8.07 (d, 2, J=7.3).

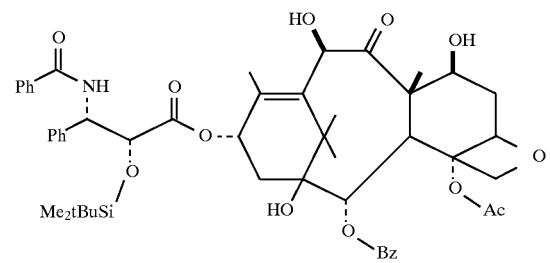

Compound III Compound II (1.0 g, 1.23 mmol) was dissolved in 5.0 mL of DMF and cooled to 0° C. To this was added Imidazole (167 mg, 2.45 mmol) and TBDMSCl (372 mg, 2.46 mmol). The reaction was allowed to regain RT and stirred overnight. The solution was transferred to a separatory funnel, diluted with EtOAc and washed with dil. NaHCO$_3$. The organic layer was separated and dried over Na$_2$SO$_4$ then filtered and the solvent removed under vacuum. The crude product was purified by column chromatography (4.8×10 cm SiO$_2$, 50:50 Hex/EtOAc) to yield 850 mg (75% yield) of compound III as a solid. ESI-MS Calcd for C$_{51}$H$_{63}$NO$_{13}$Si: 925.4. Found: 924.4 (M–H)$^+$. $^1$H NMR (300 MHz) d: −0.26 (s, 3), 0.00 (s, 3), 0.83 (s, 9), 1.11 (s, 3), 1.22 (s, 3), 1.75 (s, 3), 1.93 (s, 3), 1.83–2.44 (overlapping m, 4), 2.59 (s, 3), 3.95 (d, 1, J=7.1), 4.23–4.36 (overlapping m, 4), 4.67 (br s, 1), 4.97 (d, 1, J=7.9), 5.22 (s, 1), 5.70 (d, 1, J=7.5), 5.74 (d, 1, J=9.5) 6.31 (t, 1, J=8.9), 7.14 (d, 1, J=8.9), 7.34–7.65 (overlapping m, 11), 7.77 (d, 2, J=7.2), 8.15 (d, 2, J=7.2). $^{13}$C NMR (75MHz) 10.03, 14.39, 18.22, 21.18, 23.09, 25.60, 26.46, 36.10, 36.90, 43.20, 46.39, 55.73, 57.65, 71.56, 71.97, 74.47, 75.10, 75.20, 76.69, 78.83, 81.19, 84.33, 126.51, 127.07, 128.03, 128.80, 128.83, 129.33, 130.27, 131.90, 133.71, 134.12, 135.88, 138.36, 138.65, 166.98, 167.24, 170.25, 171.36, 210.00.

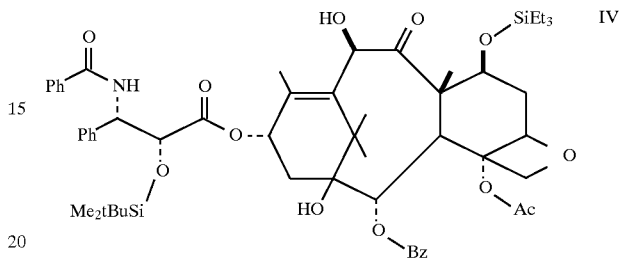

Compound IV Compound II (4.0 g, 4.32 mmol) was dissolved in 60 mL of 2:1 (v/v) CH$_2$Cl$_2$/DMF and cooled to −40° C. To this was added iPr$_2$NEt (1.79 mL, 10.32 mmol), DMAP (0.21 g, 1.72 mmol) and TESCl (1.63 mL, 9.49 mmol). The resulting reaction mixture was warmed to 0° C. and allowed to remain at that temp. overnight. The solution was then transferred to a separatory funnel, diluted with EtOAc, washed with H$_2$O (4×'s), and dried over Na$_2$SO$_4$. The solvent was removed under vacuum and the product purified by column chromatography (4.8×8 cm SiO$_2$, 6:1–3:1 Hexanes/EtOAc) to yield 3.4 g of compound IV (74 % yield) as a solid. $^1$H NMR (300 MHz) d: −0.26 (s, 3), 0.00 (s, 3), 0.57 (m, 6), 0.82 (s, 9), 0.97 (t, 9, J=8.0), 1.11 (s, 3), 1.23 (s, 3), 1.78 (s, 3), 1.96 (s, 3), 2.06–2.55 (overlapping m, 4), 2.61 (s, 3), 3.91 (d, 1, J=7.02), 4.23–4.45 (overlapping m 4), 4.69 (br s, 1), 4.97 (d, 1, J=7.7), 5.13 (s, 1), 5.68 (d, 1, J=7.1), 5.75 (dd, 1, J=1.8, 8.8), 6.34 (t, 1, J=8.7), 7.11 (d, 1, J=8.8), 7.3–7.75 (overlapping m, 11), 7.75 (d, 2, J=7.0), 8.14 (d, 2, J=7.0). $^{13}$C NMR (75 MHz) d: 5.19, 6.82, 10.22, 14.37, 18.23, 21.10, 22.71, 25.35, 26.73, 36.02, 37.73, 43.30, 46.51, 55.72, 57.83, 71.53, 72.90, 74.09, 75.10, 75.26, 76.68, 79.06, 81.14, 84.35, 126.51, 127.07, 128.76, 128.79, 129.33, 130.29, 131.84, 133.65, 134.15, 136.17, 138.19, 138.45, 166.95, 167.09, 170.34, 171.37, 209.88.

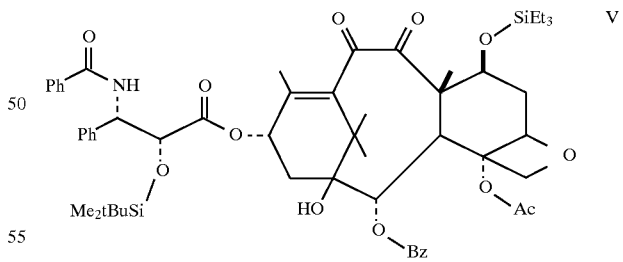

Compound V Compound IV (3.28 g, 3.15 mmol) was dissolved in 6.0 mL of 1:1 CH$_2$Cl$_2$/CH$_3$CN. To this was added 1.5 g crushed 4 Å sieves and NMO (0.55 g, 4.72 mmol). TPAP (55 mg, 0.16 mmol) was added and the reaction warmed to 40° C. After stirring 1.5 h the solvent was removed under vacuum. The resulting solid was suspended in EtOAc and filtered through a small plug of SiO$_2$ using EtOAc. The solvent was removed under vacuum. Thin layer chromatography indicated the presence of unreacted starting material. The crude reaction mixture was redissolved in 6.0 mL of 1:1 CH$_2$Cl$_2$/CH$_3$CN and resubjected to the same reaction conditions, but using 250 mg NMO and 25 mg of TPAP. The crude material was purified by column chromatography (4.8×5.0 cm SiO$_2$, 4:1 Hexanes/EtOAc) to yield 2.3 g (70% yield) of compound V as a solid. ESI-MS Calcd for C$_{57}$H$_{75}$NO$_{13}$Si$_2$: 1037.5. Found: 1036.4 (M–H)$^-$. $^1$H NMR (300 MHz) d: –0.26 (s, 3), 0.00 (s, 3), 0.60 (q, 6, J=7.7), 0.83 (s, 9), 0.99 (t, 9, J=8.0), 1.24 (s, 3), 1.26 (s, 3), 1.75 (s, 3), 1.96 (s, 3), 1.80–2.60 (overlapping m, 4), 2.61 (s, 3), 3.70 (d, 1, J=6.8), 4.204.39 (overlapping m, 3), 4.70 (br s, 1), 4.94 (d, 1, J=7.9), 5.79 (dd, 1, J=1.7, 9.25), 5.84 (d, 1, J=6.9), 6.29 (t, 1, J=8.9), 7.10 (d, 1, J=9.0), 7.32–7.76 (overlapping m, 11), 7.6 (d, 2, J=7.0), 8.17 (d, 2, J=7.0). $^{13}$C NMR (75 MHz) d: 5.31, 6.82, 8.93, 14.13, 18.21, 23.08, 23.90, 25.58, 26.92, 35.69, 37.24, 40.99, 45.77, 55.68, 58.22, 69.79, 71.21, 74.85, 75.20, 76.40, 79.33, 80.86, 84.30, 126.46, 127.04, 128.09, 128.84, 128.87, 129.10, 130.31, 131.94, 133.84, 134.07, 138.222, 142.31, 144.68, 167.00, 167.10, 170.27, 171.23, 194.19, 204.47.

Preparation of Compound VI

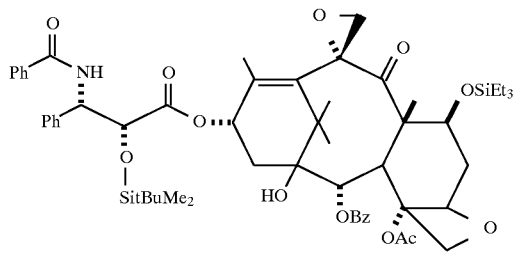

Me$_3$S$^+$I$^-$ (1.26 G, 6.15 mmol) was placed in a 25 mL Schlenk flask and suspended in 2.5 mL of THF. The suspension was cooled to –78° C. and 11.07 mL of 0.5M (PhCH$_3$) KHMDS added slowly. The resulting slurry was stirred 15 min. then warmed to 0° C. and stirred 1 h. After cooling to –78° C., compound V (1.28 g, 1.23 mmol), dissolved in 5.0 mL of THF was added dropwise over 20 min. After stirring 2 h the mixture was warmed to –40° C. and stirred for 15 min. The reaction was transferred to a separatory funnel containing 200 mL EtOAc, washed with H$_2$O (3×'s), and dried over Na$_2$SO$_4$. The solvent was removed under vacuum and the resulting mixture purified by column chromatography (4.8 cm×5.0 cm SiO$_2$, 6:1 Hexanes/EtOAc) to yield 343 mg (27% yield) of compound VI as a solid. ESI-MS Calcd for C$_{58}$H$_{77}$NO$_{13}$Si$_2$: 1051.5. Found: 1050.4 (M–H)$^+$. $^1$H NMR (500 MHz) d: –0.31 (s, 3), –0.03 (s, 3), 0.56 (m, 6), 0.79 (s, 9), 0.91 (t, 9, J=7.9), 1.11 (s, 3), 1.17 (s, 3), 1.69 (s, 3), 1.83 (m, 1), 2.02 (s, 3), 2.10 (m, 1), 2.48 (m, 1) 2.51 (overlapping m, 2), 2.56 (s, 3), 3.60 (d, 1, J=7.0), 4.16 (d, 1, J=6.7), 4.19 (d, 1, J=8.3), 4.30 (d, 1, J=8.4), 4.57 (dd, 1, J=7.0, 10.0), 4.66 (br s, 1), 4.96 (d, 1, J=8.7), 5.71 (d, 2, J=7.0), 6.12 (m, 1), 7.07 (d, 1, J=8.8), 7.28–7.58 (overlapping m, 11), 7.73 (d, 2, J=7.2), 8.11 (d, 2, J=7.3). $^{13}$C NMR (125 MHz) d: 5.14, 6.78, 10.81, 12.28, 18.19, 23.09, 25.49, 25.89, 35.50, 37.57, 42.86, 46.39, 50.35, 55.75, 61.00, 61.22, 70.35, 71.34, 75.06, 76.52, 79.01, 81.17, 84.11, 126.38, 126.95, 127.86, 128.68, 129.17, 130.16, 131.71, 132.48, 133.60, 134.10, 135.64, 138.36, 166.83, 166.94, 169.72, 171.41, 202.10. Anal calcd for: C$_{58}$H$_{77}$NO$_{13}$Si$_2$: C, 66.19; H, 7.37; N, 1.33. Found: C, 65.89; H, 7.55; N, 1.35.

Preparation of Compound Ia

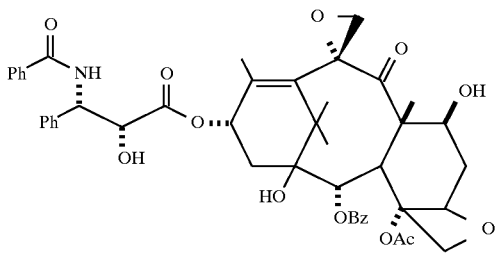

Compound VI (100 mg, 0.095 mmol) was dissolved in 2.5 mL of CH$_3$CN and cooled to 0° C. Pyridine (0.29 mL, 3.6 mmol) and 0.86 mL of HF (48%) were added. The reaction flask was stoppered and placed in the freezer (0° C.) overnight. The solution was transferred to a separatory funnel then washed with sat'd NaHCO$_3$, H$_2$O and sat'd NaCl. The organic layer was dried over Na$_2$SO$_4$. The solvent was removed and the crude product purified by column chromatography (1.4×4.0 cm SiO$_2$, 60:40 Hexanes/EtOAc) to yield 31 mg (40% yield) of compound I as a solid. ESI-MS Calcd for C$_{46}$H$_{49}$NO$_{13}$: 823.3. Found: 822.2 (M–H)$^+$. $^1$H NMR (300 MHz) d: 1.16 (s, 3), 1.22 (s, 3), 1.72 (s, 3), 1.92 (s, 3), 1.8–2.6 (overlapping m, 4), 2.38 (s, 3), 2.72 (d, 1, J=6.4), 3.63 (br s, 1), 3.76 (d, 1,J=6.4), 4.31 (m, 2), 4.31 (d, 1, J=8.4), 4.72 (dd, 1, J=7.0, 10.6), 4.79 (br s, 1), 5.01 (d, 1,J=8.6), 5.72 (d, 1, J=6.7), 5.79 (dd, 1, J=1.8, 8.9), 6.09 (t, 1, J=8.8), 7.02 (d, 1, J=7.5), 7.32–7.65 (overlapping m, 11), 7.73 (d, 2, J=7.2), 8.13 (d, 2, J=7.2).

Preparation of Compound VII

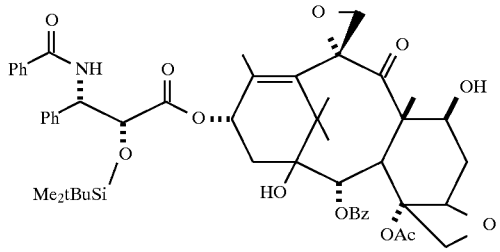

Compound VI (144 mg, 0.14 mmol) was dissolved in 2.5 mL of CH$_3$CN and cooled to 0° C. Pyridine (0.23 mL, 2.8 mmol) and 0.65 mL of HF (48%) were added and the reaction stirred 3 h. The solution was transferred to a separatory funnel then washed with sat'd NaHCO$_3$, H$_2$O, and sat'd NaCl. The organic layer was dried over Na$_2$SO$_4$. The solvent was removed and the crude product purified by column chromatography (1.4×4.0 cm SiO$_2$, 4:1 Hexanes/EtOAc) to yield 105 mg (80%) of compound VII as a solid. ESI-MS calcd for C$_{52}$H$_{63}$NO$_{13}$Si: 937.4. Found: 936.2 (M–H)$^+$.

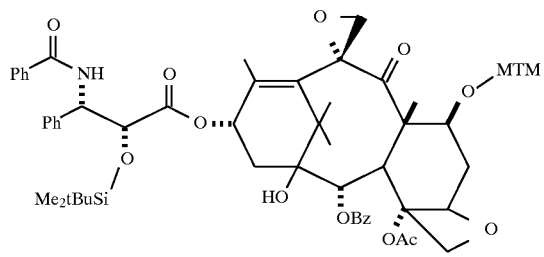

Preparation of compound VIII
Compound VII (20 mg, 0.02 mmol) was dissolved in 0.3 mL of CH$_3$CN and cooled to 0° C. DMS (0.016 mL, 0.22 mmol)

and benzoyl peroxide (24 mg, 0.10 mmol) were added and the ice-bath removed. TLC showed little reaction after 0.5 h. The reaction was re-cooled to 0° C. and additional DMS (0.042 mL, 0.58 mmol) and benzoyl peroxide (96 mg, 4 mmol) were added. After stirring 15 min. the mixture was transferred to a separatory funnel and diluted with 200 mL of $Et_2O$. The organic layer was washed with sat'd $NaHCO_3$, dried over $MgSO_4$. filtered and the solvent removed under vacuum. The crude product was purified by column chromatography (1.4×3.0 cm $SiO_2$, 4:1 Hexanes/EtOAc) to yield 16 mg of compound VIII (80% yield) as a solid. ESI-MS calcd for $C_{54}H_{67}NO_{13}SSi$: 997.4. Found: 996.4 $(M-H)^+$.

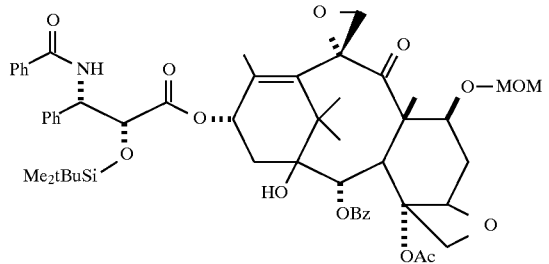

IX

Preparation of compound IX

Compound VIII (13 mg, 0.013 mmol) was dissolved in 0.5 mL of MeOH containing 4 Å mol. sieves. To this was added $I_2$ (13 mg, 0.051 mmol)) and the resulting reddish brown mixture stirred for 7 hr. Additional $I_2$ (10 mg, 0.04 mmol) was added and the reaction stirred overnight. The mixture was then transferred to a separatory funnel and diluted with EtOAc. The organic layer was washed with dil. $Na_2S_2O_3$ and $H_2O$ then dried over $Na_2SO_4$. After filtration the solvent was removed under vacuum. The crude product was purified by preparative TLC ($SiO_2$, 98:2 $CH_2Cl_2$/Acetone) to give 9 mg of compound IX (69% yield) as a solid.

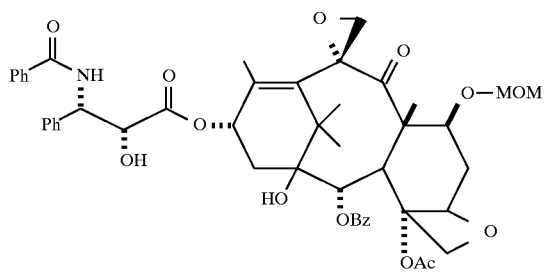

Ie

Preparation of compound Ie

Compound IX (9 mg, 0.009 mmol) was dissolved in 0.4 mL of THF and cooled to 0° C. To this was added 0.014 mL of TBAF (1.0M in THF) and the resulting solution stirred 20 min. The reaction mixture was transferred to a separatory funnel containing 100 mL of EtOAc and washed with $H_2O$ (2x's). The organic layer was dried over $Na_2SO_4$ then the solvent removed under vacuum. The crude product was purified by preparative TLC ($SiO_2$, 50:50 Hexanes/EtOAc) to give 5 mg of compound Ie. $^1H$ NMR (300 MHz) d: 1.15 (s, 3), 1.20 (s, 3), 2.38 (s, 3), 1.8–2.4 (overlapping m, 3), 2.61 (d, 1, J=6.8), 2.80 (m, 1), 3.29 (s, 3), 3.60 (br s, 1), 3.68 (d, 1, J=6.8), 4.19 (m, 2), 4.32 (d, 1, J=8.3), 4.43 (d, 1, J=7.2), 4.78 (m, 2), 4.96 (d, 1, J=8.9), 5.72 (d, 1, J=6.5), 5.81 (dd, 1, J=10.6, 1.6), 6.08 (m, 1), 7.03 (d, 1, J=9.1), 7.35–7.762 (overlapping m, 11), 7.77 (d, 2, J=7.3), 8.12 (d, 2, J=7.5).

The compounds of this invention exhibit antitumor activities in in vivo and/or in vitro models. For example, the following test describes the in vitro test used to evaluate some representative compounds of this invention.

Cytoxicity

The epoxide taxane derivatives possess cytoxicity in vitro against human colon carcinoma cells HCT-116. Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays.," Mol. Biol. Cell 3 (Suppl.):184a, 1992. Cells were plated at 4,000 cell/well in 96 well microtiter plates and 24 hours later drugs were added and serial diluted. The cells were incubated at 37° form 72 hours at which time the tetrazolium dye, MTS at 333 μg/ml (final concentration), in combination with the electron coupling agent phenazine methosulfate at 25 μM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an $IC_{50}$, which is the drug concentration required to inhibit cell proliferation (i.e. absorbance at 450 nM) to 50% of that of untreated control cells. The $IC_{50}$ values for compounds evaluated in this assay are evaluated in Table I.

TABLE I

| Compound | Cytotoxicity Assay $IC_{50}$ (nM) against HCT 116 Human colon tumor cell line[1] |
|---|---|
| Ia | 2.0 nM |
| paclitaxel* | 2.9 nM |
| Ie | 1.5 nM |
| paclitaxel* | 1.0 nM |

[1]Cytoxicity was determined after a 72 hour exposure by MTS assay.
*The assay tests comparing Ia with paclitaxel, and Ie with paclitaxel, were run on different days accounting for the difference in paclitaxel $IC_{50}$ values.

Thus, another aspect of the instant invention concerns a method for inhibiting human and/or other mammalian tumors which comprises administering to a tumor bearing host an antitumor effective amount of a compound of formula I.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mg/m² over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I, or a pharmaceutically acceptable salt thereof

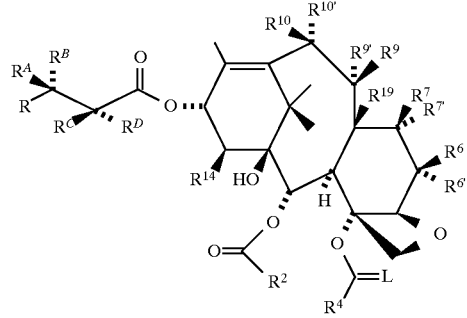

wherein:

R is phenyl, p-fluorophenyl, $C_{3-6}$ cycloalkyl, $C_{1-6}$ alkyl or $C_{1-6}$ alkenyl;

$R^A$ is hydrogen;

$R^B$ is independently —NHC(O)Ph or —NHC(O)O-($C_{1-6}$ alkyl);

$R^C$ is hydrogen;

$R^D$ is hydroxy;

$R^2$ is phenyl;

$R^4$ is methyl;

L is O;

$R^6$ and $R^{6'}$ are each hydrogen;

$R^{7'}$ is hydrogen; $R^7$ is hydrogen, hydroxy, —OCH$_2$OCH$_3$, —OCH$_2$SCH$_3$ or when taken together with $R^{19}$ forms a cyclopropane ring;

$R^9$ and $R^{9'}$ together form an oxo (keto) group;

$R^{10}$ and $R^{10'}$ together form an epoxide group which can be optionally substituted with $C_{1-6}$ alkyl;

$R^{14}$ is hydrogen; and $R^{19}$ is methyl or when taken together with $R^7$ forms a cyclopropane ring.

2. The compound of claim 1, or a pharmaceutically acceptable salt thereof wherein:

R is phenyl or p-fluorophenyl;

$R^A$ is hydrogen;

$R^B$ is independently —NHC(O)Ph or —NHC(O)OtBu;

$R^C$ is hydrogen;

$R^D$ is hydroxy;

$R^2$ is phenyl;

$R^4$ is methyl;

L is O;

$R^6$ and $R^{6'}$ are each hydrogen;

$R^{7'}$ is hydrogen; $R^7$ is hydroxy, —OCH$_2$OCH$_3$ or —OCH$_2$SCH$_3$;

$R^9$ and $R^{9'}$ together form an oxo (keto) group;

$R^{10}$ and $R^{10'}$ together form an epoxide group which can be optionally substituted with $C_{1-6}$ alkyl;

$R^{14}$ is hydrogen; and $R^{19}$ is methyl.

3. The compound of claim 2 having the formula Ia or a pharmaceutically acceptable salt thereof,

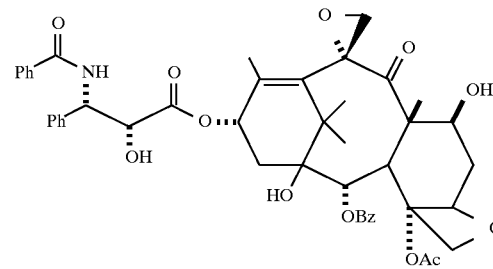

4. The compound of claim 2 having the formula Ib or a pharmaceutically acceptable salt thereof,

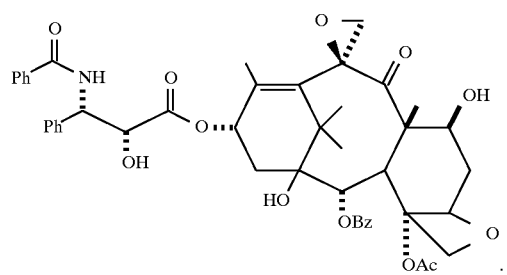

5. The compound of claim 2 having the formula Ic, or a pharmaceutically acceptable salt thereof,

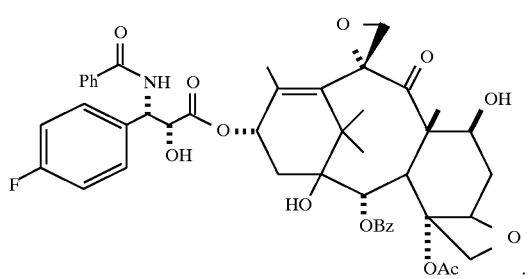

6. The compound of claim 2 having the formula Id, or a pharmaceutically acceptable salt thereof,

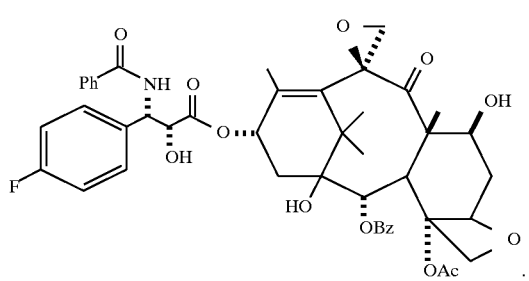

7. The compound of claim 2 having the formula Ie, or a pharmaceutically acceptable salt thereof,

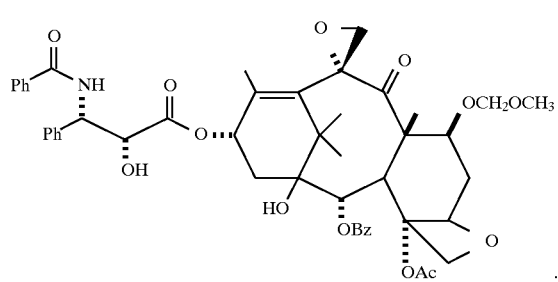

8. The compound of claim 2 having the formula If, or a pharmaceutically acceptable salt thereof,

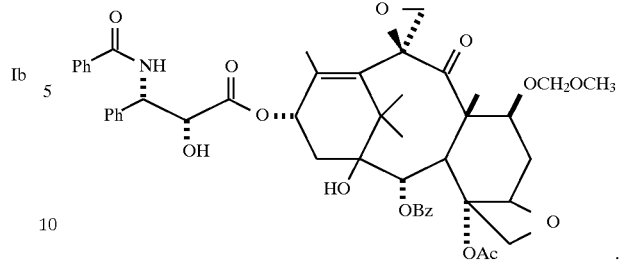

9. The compound of claim 2 having the formula Ig, or a pharmaceutically acceptable salt thereof,

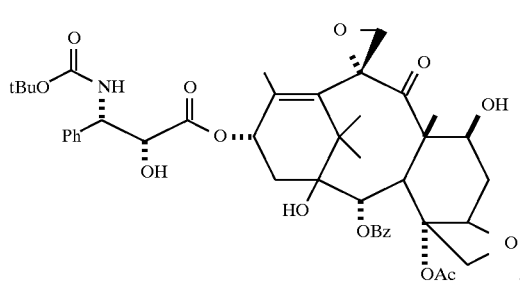

10. A compound of claim 2 having the formula Ih, or a pharmaceutically acceptable salt thereof,

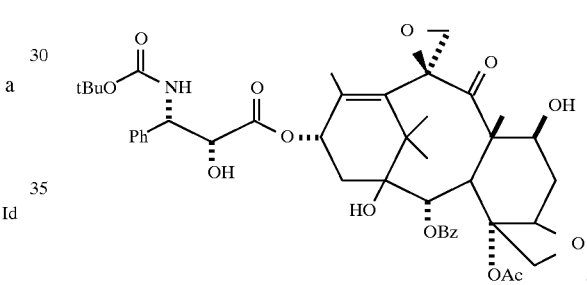

11. The compound of claim 1 having the formula Ij, or a pharmaceutically acceptable salt thereof,

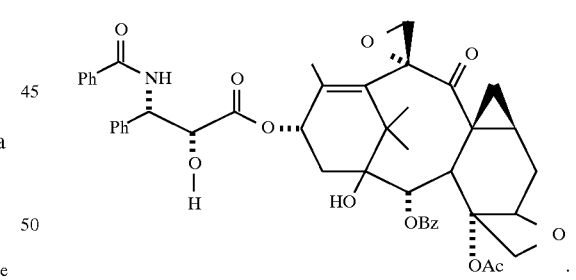

12. The compound of claim 1 having the formula Ik, or a pharmaceutically acceptable salt thereof,

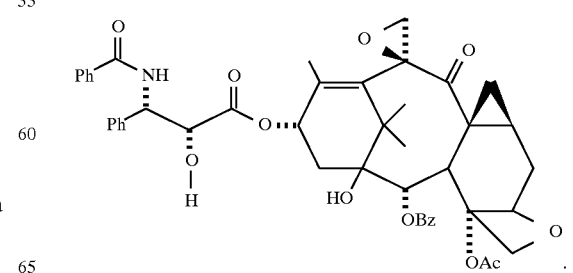

13. The compound of claim 1 having the formula Im, or a pharmaceutically acceptable salt thereof,

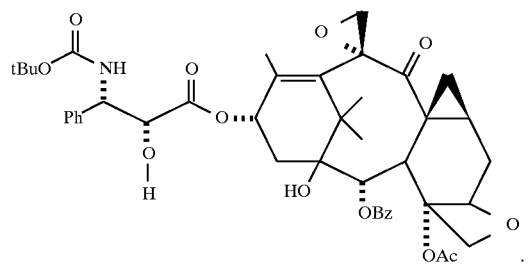

14. The compound of claim 1 having the formula In, or a pharmaceutically acceptable salt thereof,

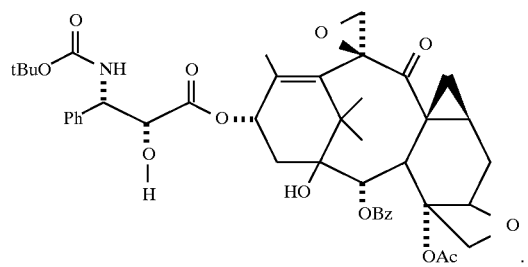

15. The compound of claim 1 having the formula Io or a pharmaceutically acceptable salt thereof,

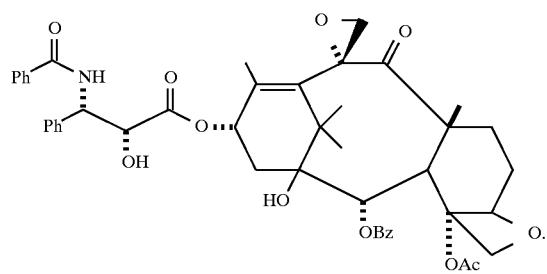

16. The compound of claim 1 having the formula Ip or a pharmaceutically acceptable salt thereof,

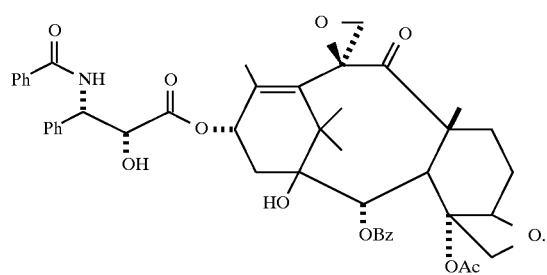

17. The compound of claim 1 having the formula Iq, or a pharmaceutically acceptable salt thereof,

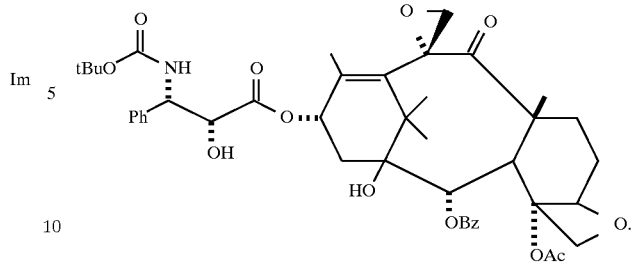

18. The compound of claim 1 having the formula Ir, or a pharmaceutically acceptable salt thereof,

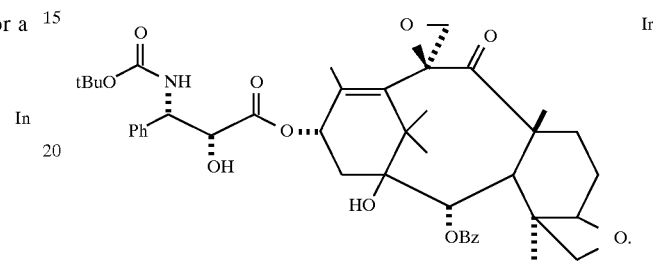

19. The compound of claim 2 having the formula Is, or a pharmaceutically acceptable salt thereof,

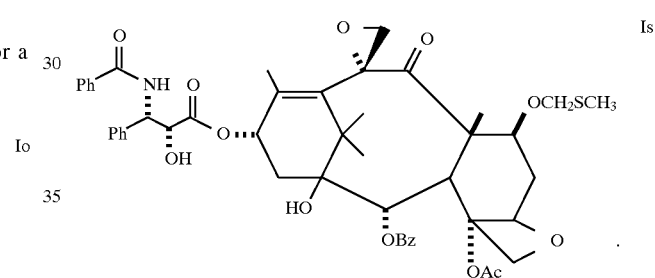

20. The compound of claim 2 having the formula It, or a pharmaceutically acceptable salt thereof,

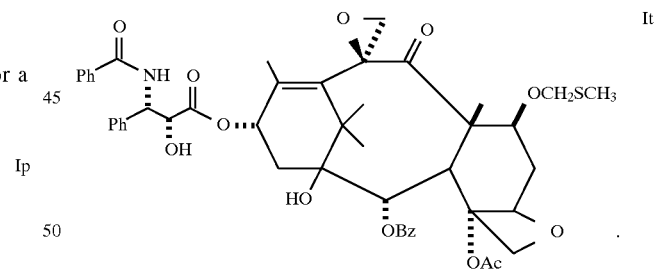

21. A pharmaceutical formulation which comprises an antitumor effective amount of a compound of formula I as claimed in any one of claims 1–20.

22. A method for inhibiting tumor growth in a mammalian host which comprises administering to said mammal a tumor-growth inhibiting amount of a compound of formula I as claimed in any one of claims 1–20.

* * * * *